United States Patent [19]

Suzuki et al.

[11] Patent Number: 5,157,452
[45] Date of Patent: Oct. 20, 1992

[54] METHOD AND APPARATUS FOR LIQUID CONTENT DETECTION WITH REFRACTIVE INDEX AND TEMPERATURE SIGNAL MIXING

[75] Inventors: Hiroyoshi Suzuki; Kenji Ogawa, both of Himeji, Japan

[73] Assignee: Mitsubishi Denki Kabushiki Kaisha, Tokyo, Japan

[21] Appl. No.: 723,884

[22] Filed: Jul. 1, 1991

[30] Foreign Application Priority Data

Jul. 3, 1990 [JP] Japan .................................. 2-174480
Jul. 9, 1990 [JP] Japan .................................. 2-179458

[51] Int. Cl.⁵ .......................................... G01N 21/41
[52] U.S. Cl. .................................... 356/128; 356/133
[58] Field of Search ............... 356/128, 133, 135, 136, 356/137; 250/227.14; 123/1 A, 494

[56] References Cited

U.S. PATENT DOCUMENTS

| | | | |
|---|---|---|---|
| 4,438,749 | 3/1984 | Schwippert | 356/133 |
| 4,749,274 | 6/1988 | Aoki et al. | 356/136 |
| 5,015,091 | 5/1991 | Suzuki et al. | 356/135 |

FOREIGN PATENT DOCUMENTS

| | | | |
|---|---|---|---|
| 2642891 | 3/1978 | Fed. Rep. of Germany | 356/135 |
| 171350 | 5/1989 | Japan . | |
| 207648 | 8/1989 | Japan | 356/136 |

Primary Examiner—F. L. Evans
Attorney, Agent, or Firm—Sughrue, Mion, Zinn, Macpeak and Seas

[57] ABSTRACT

A refractive index sensor senses the refractive index of a mixed liquid and generates a corresponding signal. A temperature sensor senses the temperature of the liquid and generates a corresponding signal. A signal mixer mixes the refractive index signal and the temperature signal with each other to provide a single mixed signal which is then fed through a single signal line to a liquid content calculator where the sensed refractive index is modified based on the sensed liquid temperature to provide a temperature compensated refractive index from which the content of a liquid component in the liquid is calculated. This simplifies the arrangement of the entire apparatus and improves the operational reliability thereof as compared with the case in which the two signals are separately supplied to the liquid content calculator through two signal supply systems.

8 Claims, 13 Drawing Sheets

_METHOD AND APPARATUS FOR LIQUID CONTENT DETECTION WITH REFRACTIVE INDEX AND TEMPERATURE SIGNAL MIXING_

BACKGROUND OF THE INVENTION

The present invention relates to a liquid content detecting apparatus and a method for detecting the content of a liquid component contained in a liquid mixture such as a mixed fuel in a contactless manner.

In recent years, a fuel comprising gasoline mixed with alcohol has become popular for automotive use in many countries including the United States of America, European countries, etc., for the purpose of reducing the consumption of petroleum.

If, however, such an alcohol-mixed fuel is used for engines suited to a gasoline fuel which forms an air fuel mixture having a stoichiometric air/fuel ratio for the proper combustion thereof, the air/fuel ratio of a mixture formed of the alcohol-mixed fuel becomes leaner than that with the gasoline fuel due to the fact that the stoichiometric air/fuel ratio is much lower with a fuel containing alcohol than with a gasoline fuel containing no alcohol. For this reason, the content of alcohol in an alcohol-mixed fuel is detected so that engine control parameters are controlled in accordance with the alcohol content thus detected to properly adjust the air/fuel ratio, fuel injection timing, ignition timing, etc., so as to provide good combustion thereof.

Examples of conventional liquid content detecting apparatuses for detecting the content of alcohol in a mixed fuel based on the refractive index thereof are disclosed in Japanese Utility Model Application Laid-Open No. 62-81064, Japanese Patent Application Laid-Open Nos. 1-262442 and 1-263536, etc. In these examples, however, the temperature dependencies of the refractive indexes of gasoline and alcohol are different from each other, as shown in FIG. 13. Therefore, in order to accurately detect the content of alcohol in an alcohol-mixed fuel, it is necessary to sense the temperature of the fuel and modify the refractive index thereof based on the thus sensed fuel temperature. Thus, the refractive index and the temperature of the fuel are sensed and input to an engine control unit (ECU) in the form of a microcomputer.

FIG. 14 shows the general arrangement of a liquid content detecting apparatus disclosed in Japanese Utility Model Application Laid-Open No. 1-171350. Here, let us assume that a fuel to be detected is an alcohol-mixed fuel comprising a first liquid in the form of alcohol and a second liquid in the form of a gasoline. In FIG. 14, the conventional liquid content detecting apparatus includes a refractive index sensor, which is generally designated by reference numeral 101, for sensing the refractive index of a liquid fuel in a contactless manner, a refractive index calculator 102 for calculating the refractive index of the fuel based on the output signal of the sensor 101, a temperature sensor 103 for sensing the temperature of the fuel in the refractive index sensor 101 and generating a corresponding output signal, and an refractive index modifying means 104 for calculating the content of an alcohol contained in the fuel.

As shown in detail in FIG. 14, the refractive index sensor 101 includes a casing 115 at opposite ends of which a light emitter 111 and a light receiver 113 are disposed in an opposed, face-to-face relation so that light L emitted from the light emitter 111 passes through a cylindrical light guide 112 towards the light receiver 113.

The casing 115 has a hollow interior in the form of a fuel passage 116, an inlet port 118 for introducing a liquid fuel into the fuel passage 116, and an outlet port 119 for discharging the fuel from the fuel passage 116 to the outside. Thus, a fuel enters the casing 115 from the inlet port 118, flows around the cylindrical light guide 112 in the flow passage 116, and exits the casing 115 from the outlet port 119.

The outer peripheral surface of the cylindrical light guide 112 is sealingly supported at its opposite ends by the opposite end walls of the casing 115 through a pair of annular seals 114 which serve to prevent the leakage of fuel from the interior of the casing 115 towards the outside through the outer periphery of the light guide 112 and the opposite end walls of the casing 115.

The refractive index calculator 102 is connected to the light emitter 111 and the light receiver 113 for calculating the refractive index of the fuel in the fuel passage 116 in the casing 115 based on the output signal from the light receiver 113 and generating a corresponding output signal to the refractive index modifying means 104. Specifically, the refractive index calculator 102 calculates the refractive index of the fuel on the basis of a change or difference between the amount of light emitted from the light emitter 111 and that received by the light receiver 113.

The temperature sensor 103 in the form of a thermistor is mounted on the casing 115 for sensing the temperature of the fuel in the fuel passage 116 in the casing 115 and generating a corresponding output signal to the refractive index modifying means 104.

Based on the output signal of the refractive index calculator 102 and the output signal of the temperature sensor 103, the refractive index modifying means 104 calculates the content of an alcohol contained in the fuel in the fuel passage 116.

FIG. 15 shows, in a block diagram, a concrete example of the refractive index modifying means 104. In this figure, a resistor 141 is connected in parallel to the temperature sensor 103, and an operational amplifier 142 has a first negative or inverted input terminal connected to one end of the resistor 141, a second positive or non-inverted input terminal connected to a power supply 143, and an output terminal connected to the other end of the resistor 141. The operational amplifier 142 functions as a non-inverting amplifier in relation to the output voltage Vo of the power supply 143. A resistor 144 has one end thereof connected to the first inverted input terminal of the operational amplifier 142 and the other end thereof connected to ground. An operational amplifier 145 has a first negative or inverted input terminal connected to the output terminal of the operational amplifier 142 through a resistor and to the refractive index calculator 102 through a resistor, and a second positive or non-inverted input terminal connected to ground. An operational amplifier 146 has a first negative or inverted input terminal connected to both the output terminal and the first inverted input terminal of the operational amplifier 145 through respective resistors, a second positive or non-inverted input terminal connected to ground, and an output terminal connected to the first inverted input terminal thereof through a resistor. The operational amplifier 146 generates an output signal VCa representative of the content of alcohol at its output terminal. The operational amplifiers 145, 146 function as inverting amplifiers in relation to signals input to the first inverted input terminals thereof.

FIG. 16 shows the output characteristic of the refractive index calculator 102 in which a refractive index signal VND changes linearly with respect to the refractive index NDf of the alcohol-mixed fuel. Though not illustrated, the refractive index NDf of the fuel is a linear function of the alcohol content Ca and it is thus equivalent to the alcohol content.

FIG. 17 shows the relationships between the temperature T and the resistance RS of the temperature sensor 103 and between the temperature T and the total resistance RP of the temperature sensor 103 including the resistor 141, in which the resistance RS of the temperature sensor 103 alone changes non-linearly with respect to the temperature T thereof, while the total resistance RP of the temperature sensor 103 and the resistor 141 changes substantially linearly with respect to the temperature T thereof.

FIG. 18 shows the relationships between the temperature T and the refractive index NDg of gasoline and between the temperature T and the refractive index NDa of alcohol, in which temperature coefficients $\alpha g$, $\alpha a$ for the refractive indexes NDg, NDa are different from each other.

FIG. 19 shows the relationship of the temperature T and the refractive index Ca of alcohol, which represents a temperature modification error or tolerance in the case where the content of alcohol Ca is calculated based on an alcohol content signal VCa which is modified to a value at a reference temperature To.

The operation of the above-described liquid content detecting apparatus as shown in FIGS. 14 and 15 will be described below with particular reference to FIGS. 16 through 19. First, as shown in FIG. 14, the light emitter 111 emits beams of light L into the cylindrical light guide 112 at a large conical angle, which are refracted at the interface or boundary surface between the fuel, whose refractive index is NDf, in the fuel passage 116 in the casing 115 and the outer peripheral surface of the cylindrical light guide 112, whose refractive index is NDr, at angles of refraction which depend on the angles of incidence of the respective light beams L. Thus, part of the light L from the light emitter 111 is refracted at the boundary surface and enters the body of fuel in the fuel passage 116, whereas the remaining portion of the light L is reflected at the boundary surface back into the interior of the cylindrical light guide 112 and received by the light receiver 113.

In this regard, the critical or minimum angle of incidence, at which the light beams L from the light emitter 111 incident to the boundary surface are totally reflected into the interior of the cylindrical light guide 112, is called the angle of total reflection $\theta r$, and there is the following relationship between the angle of total reflection $\theta r$ and the refractive indexes NDf, NDr of the fuel and the light guide 112:

$$\sin \theta r = NDf/NDr$$

Therefore, all the light beams L having angles of incidence greater than the angle of total reflection $\theta r$ are reflected at the boundary surface into the interior of the light guide 112 and received by the light receiver 113.

The refractive index NDf of the alcohol-mixed fuel varies in accordance with the content of alcohol Ca therein, so the angle of total reflection $\theta r$ accordingly changes with the alcohol content Ca. Thus, the amount of light L received by the light receiver 113 changes in dependence upon the alcohol content Ca in the fuel. For this reason, the light receiver 113 comprises an element such as a phototransistor which generates an electric current having a magnitude proportional to the amount of light L received. The current thus generated is input to the refractive index calculator 102 where it is converted into a corresponding voltage which is proportional to the amount of light L received by the light receiver 113.

Now, let us consider the case in which the fuel to be detected comprises gasoline mixed with an alcohol in the form of methanol; the cylindrical light guide 112 is formed of an optical glass BK7 having a refractive index of 1.52; and the temperature Tf of the fuel sensed by the temperature sensor 103 is room temperature, i.e., 20° C. In this case, the angle of total reflection $\theta r$ of gasoline (i.e., a fuel comprising 100% gasoline containing no methanol (M0)), which has a refractive index of about 1.42 at room temperature, is about 69 degrees, whereas that of methanol (i.e., a fuel comprising 100% methanol containing no gasoline (M100)), which has a refractive index of 1.33 at room temperature, is 49 degrees. That is, the higher the alcohol content Ca in gasoline, the lesser the refractive index NDf of the alcohol-mixed fuel and hence the angle of total reflection $\theta r$ become. Therefore, as the alcohol content Ca in gasoline increases, beams of light L projected from the light emitter 111 at an increasing conical angle of projection can reach the light receiver 113, so the amount of light L received by the light receiver 113 increases. As a result, the output VND of the refractive index calculator 102 decreases in inverse proportion to the increasing refractive index NDf of the fuel, as clearly seen from FIG. 16.

Since the refractive index VD is in inverse proportion to the temperature T, as shown in FIG. 18, the refractive index modifying means 104 modifies the output VND of the refractive index calculator 102 in the following manner.

First, the temperature dependency of the resistance RS of the temperature sensor 103, which is non-linear as shown in FIG. 17, is modified to be substantially linear by connecting the resistor 141 in parallel to the temperature sensor 103, so that the total resistance RP of the temperature sensor 103 and the resistor 141 varies linearly with respect of the temperature thereof. That is, the total resistance RP is expressed by the following equations:

$$\begin{aligned} RP &= RS \times R1/(RS + R1) \\ &= RP_o\{1 - \beta(Tf - To)\} \end{aligned} \quad (1)$$

where RS is the resistance of the temperature sensor; R1 is the resistance of the resistor 141; T° is a prescribed reference temperature; RP° is the total resistance of the temperature sensor 103 and the resistor 141 at the reference temperature T°; and $\beta$ is a temperature coefficient of the total resistance RP.

From equation (1) above, the temperature signal VT output from the operational amplifier 142 is given by the following equation:

$$VT = VO\{(1 + RP^\circ/R2) - \{RP^\circ \times \beta(Tf - T^\circ)/R2\} \quad (2)$$

where Vo is the output voltage of the power supply 143; and R2 is the resistance of the resistor 144.

The temperature output signal VT from the operational amplifier 142 is combined with the refractive index signal VND from the refractive index calculator 102 and together fed to the operational amplifier 145 where they are amplified and fed to the operational amplifier 146 which generates a positive output voltage in the form of an alcohol content signal VCa. Here, the refractive index signal VND is expressed as follows:

$$VND = VND° - K \times NDf\{1 - a(TF - T°)\} \quad (3)$$

where VND° is the refractive index of the fuel at the reference temperature T°; K is an output gain of the refractive index calculator 102; and α is a temperature coefficient of the refractive index NDf.

From equation (3) above, by adjusting the resistance R1 of the resistor 141, the total resistance RP° at the reference temperature T° can be changed in an appropriate manner. Also, from equation (2) above, the temperature coefficient $\beta$VT of the temperature signal VT is given as follows:

$$\beta_{\text{VT}} = Vo \times RP° \times \beta/R2$$

In addition, from equation (3) above, the temperature coefficient αVND of the refractive index signal VND is given as follows:

$$\alpha VND = K \times NDf \times \alpha$$

Accordingly, by adjusting the resistance R1 of the resistor 141 and the resistance R2 of the resistor 144, the temperature coefficients $\beta$VT, αVND for an optimal value of the total resistance RP°, which is in advance set to be substantially linear, can be made equal to each other. As a result, the temperature coefficient of the alcohol content signal VCa is removed to provide a temperature-compensated refractive index NDf and an alcohol content Ca.

In fact, however, since the temperature coefficient αg of the refractive index NDg of gasoline is different from that αa of the refractive index NDa of alcohol, temperature compensation can be made only for one point in the alcohol content. Thus, for example, the alcohol content Ca calculated from the alcohol content signal VCa can be temperature compensated only for an alcohol content of around 50%, and it still has temperature dependency for all other ranges of the alcohol content and does not become constant irrespective of the temperature T.

With the conventional liquid content detecting apparatus a described above, in which the refractive index modifying means 104 comprises the resistor 141 and the operational amplifier 142 both connected to the temperature sensor 103, it is possible to perform temperature compensation only for a certain alcohol content, and an error results due to variations in temperature for other alcohol content ranges. Thus, it is impossible to accurately detect the content of alcohol at all times over the entire temperature range in which the fuel is used.

In addition, the above-mentioned conventional apparatus has another problem. That is, two signals, one in the form of the output signal VND from the refractive index calculator 102 and the other in the form of the output signal Tf from the temperature sensor 103, are required to be input to the refractive index modifying means 104 for modifying the refractive index VND as calculated by the refractive index calculator 102 on the basis of the temperature signal Tf from the temperature sensor 103, so that two signal lines, two connectors and the like are required for these two signals. This results in a complicated wiring arrangement and deterioration in reliability of the device due to increased possibilities of noise interference, failure, etc.

SUMMARY OF THE INVENTION

Accordingly, the present invention is intended to overcome the above-described problems of the conventional liquid content detecting apparatus.

It is an object of the invention to provide a novel and improved liquid content detecting apparatus and method which can accurately detect the content of a liquid component in a liquid at all times irrespective of the temperature of the liquid, by compensating or modifying the sensed refractive index based on the sensed temperature of the liquid over a wide operating temperature range without regard to the liquid content.

It is another object of the invention to provide a novel and improved liquid content detecting apparatus and method which is highly reliable in operation by employing a single signal line through which a refractive index signal and a temperature signal are supplied as a mixed signal to a liquid content calculator.

In order to achieve the above objects, according to one aspect of the invention, there is provided a liquid content detecting apparatus for detecting the content of a liquid component contained in a mixed liquid. The apparatus comprising:

a refractive index sensor for sensing the refractive index of a liquid component in the mixed liquid and generating a corresponding refractive index signal;

a temperature sensor for sensing the temperature of the mixed liquid and generating a corresponding temperature signal;

a signal mixer for mixing the refractive index signal and the temperature signal with each other to generate a single mixed signal; and a liquid content calculator for calculating the content of the liquid component based on the mixed signal.

In one form, the refractive index signal and the temperature signal are both of analog form. In this case, it is preferable that the signal mixer comprise: a first operational amplifier connected to receive one of the refractive index signal from the refractive index sensor and the temperature signal from the temperature sensor, the first operational amplifier being operable to maintain the analog form of one of the signals received; a second operational amplifier connected to receive the other of the refractive index signal and the temperature signal for converting the other signal from analog into digital form; and an analog switch having an input terminal connected to the first operational amplifier, a control terminal connected to the second operational amplifier, and an output terminal connected to the liquid content calculator, the analog switch being opened and closed by a digital signal output from the second operational amplifier.

In another form, the refractive index signal and the temperature signal are both of analog form. In this case, it is preferable that the signal mixer comprise: a first operational amplifier connected to receive one of the refractive index signal from the refractive index sensor and the temperature signal from the temperature sensor, the first operational amplifier being operable to maintain the analog form of one of the signals received; a second operational amplifier connected to receive the other of the refractive index signal and the temperature signal for converting the other signal from analog into digital form; a third amplifier having an input terminal connected through a resistor to the first operational amplifier and an output terminal connected to the liquid content calculator; and an analog switch connected to a node between the resistor and the third amplifier, a control terminal connected to the second operational amplifier, and an output terminal connected to ground, the analog switch being opened and closed by a digital signal output from the second operational amplifier so as to permit and interrupt the transmission of the analog signal from the first operational amplifier to the third amplifier.

Preferably, the liquid content calculator comprises: a signal separator for generating a refractive index component corresponding to the refractive index signal and a temperature component corresponding to the temperature signal; and refractive index modifying and liquid content calculating means for modifying the sensed refractive index of the liquid from the refractive index sensor based on the temperature signal from the temperature sensor to provide a temperature compensated refractive index of the liquid, the refractive index modifying and liquid content calculating means being operable to calculate the content of each liquid component based on the temperature compensated refractive index.

Preferably, the signal separator has a single input terminal connected to receive the mixed signal from the signal mixer, a first output terminal directly connected to the input terminal through a signal line for outputting the mixed signal as an analog component, and a second output terminal connected to the input terminal through a comparator, the comparator generating a digital component depending upon whether the mixed signal is higher or lower than a prescribed threshold.

In a preferred form, the signal mixer comprises: a first amplifier for receiving the refractive index signal in analog form from the refractive index sensor and converting it into a first digital signal; a second amplifier for receiving the temperature signal in analog form from the temperature sensor and converting it into a second digital signal, the first and second digital signals being opposite in polarity from each other; a first analog switch having an input terminal connected to receive the first digital signal from the first amplifier an output terminal and a control terminal; a second analog switch having an input terminal connected to receive the second digital signal from the second amplifier, an output terminal and a control terminal; an operational amplifier having a first inverted input terminal connected through a resistor to the output terminals of the first and second analog switches, a second non-inverted input terminal connected to ground, and an output terminal connected through a capacitor to the first inverted input terminal thereof; and a comparator having an input terminal connected to a junction between the output terminal of the operational amplifier and the capacitor for receiving an output signal from the operational amplifier which is integrated by the capacitor, and an output terminal connected to the control terminal of the first analog switch and to the control terminal of the second analog switch through an inverter so that the first and second analog switches are alteratively opened and closed by the output signal from the comparator, the comparator having an upper threshold and a lower threshold so that it serves to invert, with hysteresis, the integrated output signal from the operational amplifier so as to be within a range between the upper and lower thresholds, to provide a mixed signal.

In a preferred form, the refractive index modifying means comprises: memory means for storing a reference refractive index and a modification coefficient at a predetermined reference temperature for each of the liquid components; refractive index calculating means for calculating the refractive index of each liquid component at the temperature of the liquid as sensed by the temperature sensor using the reference refractive index and the modification coefficient at the predetermined temperature for the corresponding liquid component; and interpolation means for calculating an actual refractive index of each liquid component based on the primary refractive index thereof sensed by the refractive index sensor and the estimated refractive index thereof calculated by the refractive index calculating means.

In another aspect of the invention, there is provided a liquid content detecting method comprising the steps of:

sensing the temperature of the liquid and generating a corresponding temperature signal;

sensing the refractive index of the liquid and generating a corresponding refractive index signal;

reading a reference refractive index and a modification coefficient at a predetermined temperature for each liquid component of the liquid;

calculating the temperature compensated refractive index of each liquid component at the sensed temperature of the liquid on the basis of the reference refractive index and the modification coefficient therefor thus read; and calculating the content of each liquid component based on the temperature compensated refractive index thereof.

The above and other objects, features and advantages of the invention will become more readily apparent from the following detailed description of a few preferred embodiments of the invention taken in conjunction with the accompanying drawings.

BRIEF DESCRIPTION OF THE DRAWINGS

FIG. 6 is a block diagram showing a concrete example of a refractive index modifying means of FIG. 1;

In the drawings, the same or corresponding parts are identified by the same symbols.

DESCRIPTION OF THE PREFERRED EMBODIMENTS

A few preferred embodiments of the present invention will now be described in detail while referring to the accompanying drawings. In the following, for the sake of simplification in the description, the present invention will be described as applied to detecting the content of a fuel component in a fuel which is used in an automotive engine.

Figure 1:
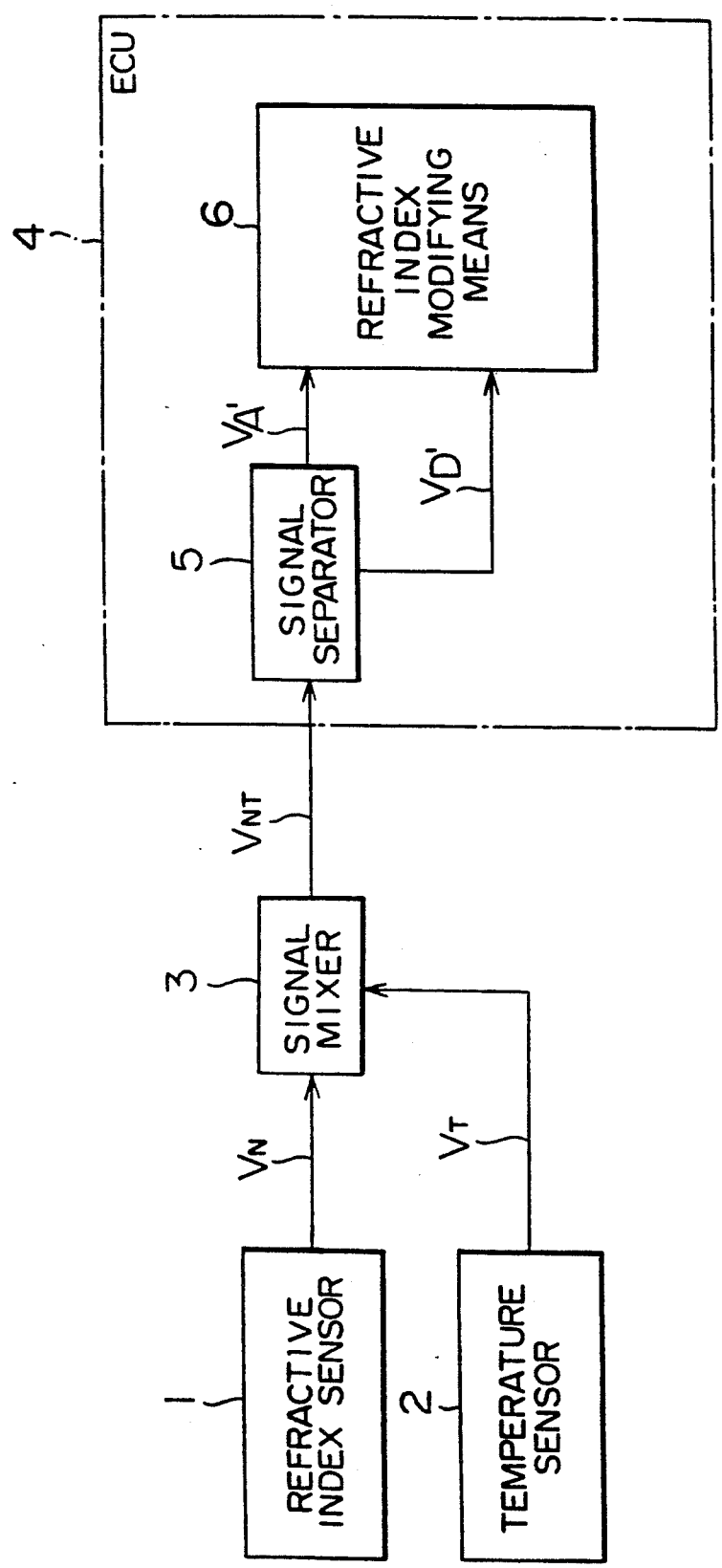
FIG. 1 is a block diagram showing the general construction of a liquid content detecting apparatus in accordance with the invention.
Figure 14:
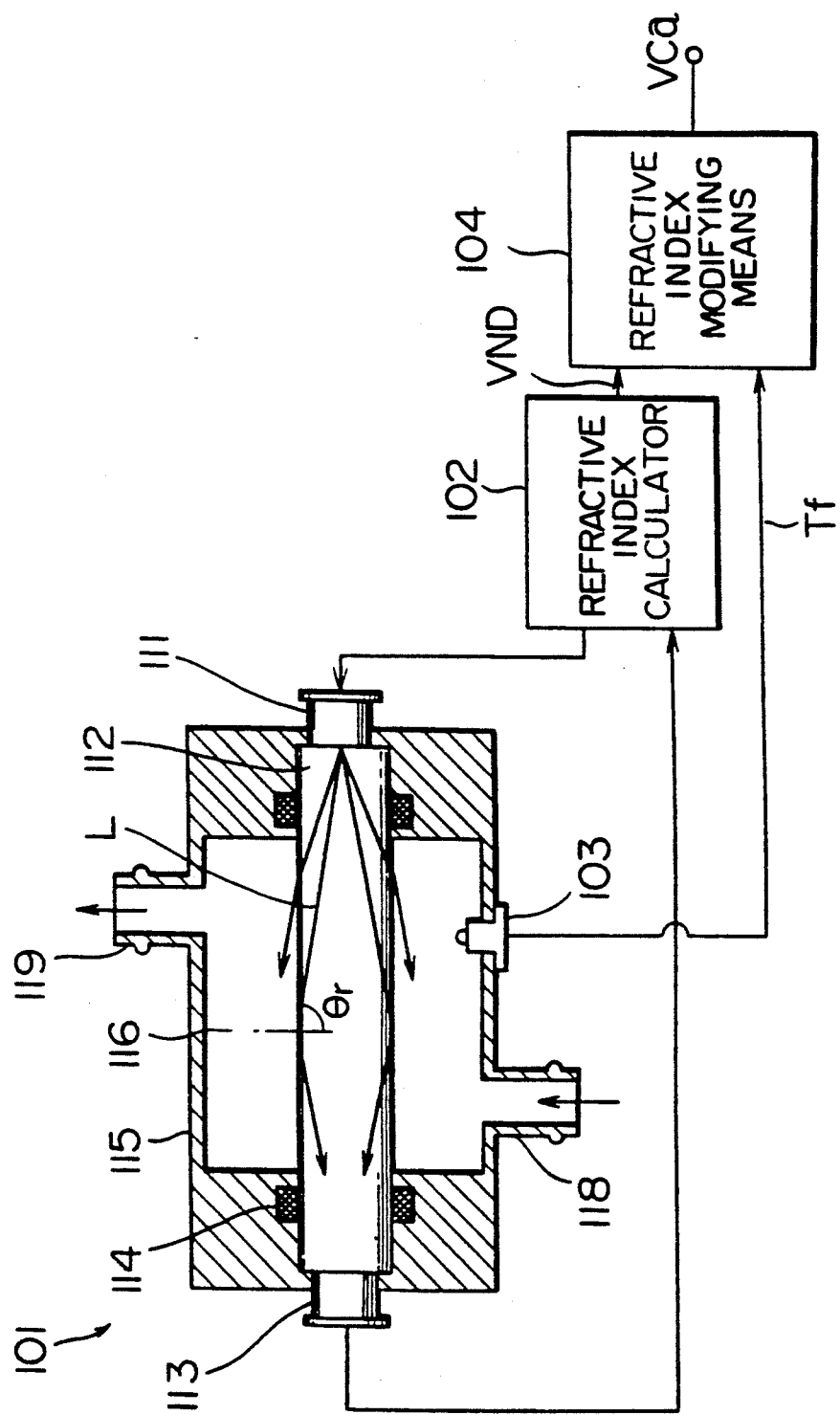
FIG. 14 shows a conventional liquid content detecting apparatus with a refractive index sensor illustrated in a vertical section.
Figure 15:
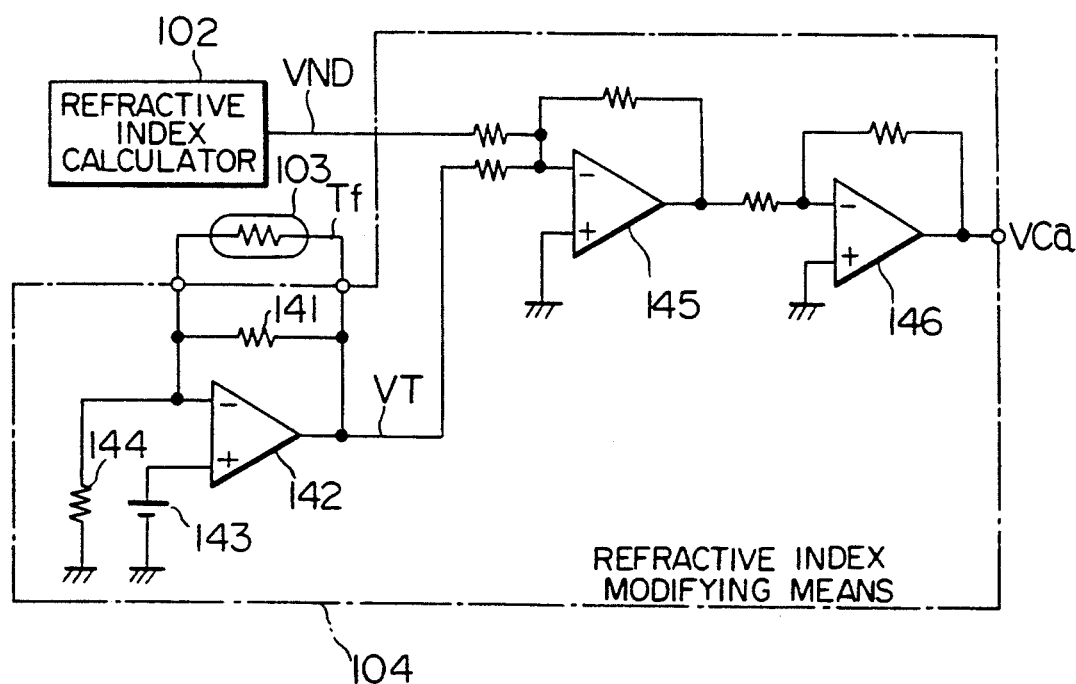
FIG. 15 is a circuit diagram of a concrete example of a refractive index modifying means of FIG. 14.

Referring first to FIG. 1, there is shown a liquid content detecting apparatus constructed in accordance with a first embodiment of the invention. The device illustrated includes a refractive index sensor 1 for sensing the refractive index of a liquid, which is, in this embodiment, in the form of a fuel comprising gasoline and alcohol, and generating a corresponding output signal $V_N$ in analog form, a temperature sensor 2 for sensing the temperature of the liquid in the refractive index sensor 1 and generating a corresponding output signal $V_T$ in analog form, a signal mixer 3 for mixing the output signal $V_N$ of the refractive index sensor 1 and the output signal $V_T$ of the temperature sensor 2 to generate a combined or mixed signal $V_{NT}$, and a liquid content calculator 4 in the form of an engine control unit (ECU) for calculating the content of a liquid component in the liquid based on the output signal $V_{NT}$ from the refractive index sensor 1. In this embodiment, the refractive index sensor 1 and the temperature sensor 2 may be the same as the elements 101 and 103, respectively, of FIG. 14, but the liquid content calculator 4 includes a signal separator 5 for separating a refractive index component $V_N$ and a temperature component $V_T'$ from the mixed output signal $V_{NT}$ of the signal mixer 3, and a refractive index modifying means 6 for modifying the refractive index as sensed by the refractive index sensor 1 on the basis of the liquid temperature as sensed by the temperature sensor 2.

Figure 2:
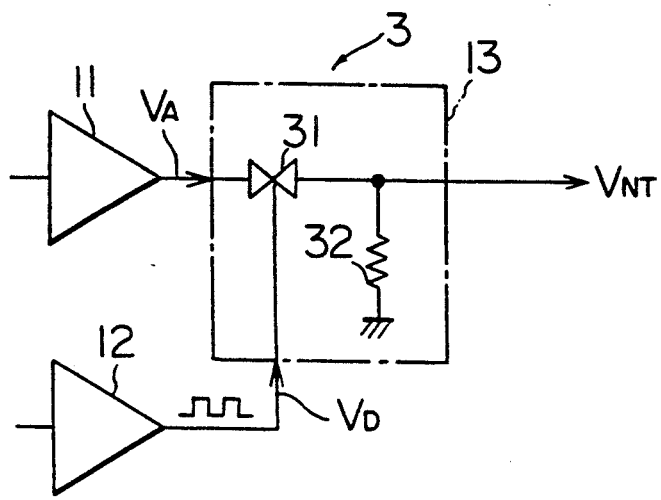
FIG. 2 is a circuit diagram of one example of a signal mixer of FIG. 1.

FIG. 2 shows a concrete example of the signal mixer 3. In this example, the mixer 3 includes a first amplifier 11 for amplifying the analog output signal $V_N$ from the refractive index sensor 1 to generate an amplified analog output $V_A$, a second amplifier 12 in the form of an analog/digital (A/D) converter for amplifying and converting the analog output signal $V_T$ from the temperature sensor 2 into a digital signal $V_D$, and a mixing means 13 for mixing the analog signal $V_A$ and the digital signal $V_D$. For example, the output signal $V_T$ from the temperature sensor 2 can be a voltage signal which is converted into a corresponding frequency by the A/D converter 12 in the form of a voltage/frequency (V/F) converter. In this regard, the first amplifier 11 may instead be an A/D converter for converting the analog output signal $V_N$ into a digital signal, while the second amplifier 12 does not perform A/D conversion. The mixing means 13 comprises an analog switch 31 which has an input terminal connected to the first amplifier 11, a control terminal connected to the second amplifier 12, and an output terminal connected to the signal separator 5. The analog switch 31 operates to selectively allow and stop the passage of the analog signal $V_A$ input from the first amplifier 11 to its input terminal in response to the digital signal $V_D$ imposed upon its control terminal from the second amplifier 12, so that it generates a combined or mixed output signal to the signal separator 3. A resistor 32 is connected between the output terminal of the analog switch 31 and ground.

Figure 3:
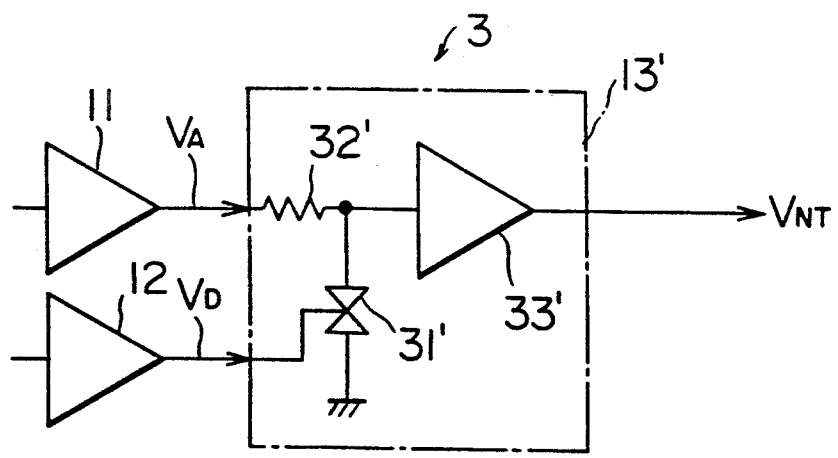
FIG. 3 is a circuit diagram of another example of a signal mixer of FIG. 1.

FIG. 3 shows another example of the signal mixer 3 which is similar to the FIG. 2 embodiment except for the construction of a mixing means 13'. In this example, the mixing means 13' comprises an analog switch 31' which has an input terminal connected through a resistor 32' to a first amplifier 11, a control terminal connected to a second amplifier 12 and an output terminal connected to ground, and a buffer amplifier 33' which has an input terminal connected to a junction between the analog switch 31' and the resistor 32'. and an output terminal connected to the signal separator 5. The analog switch 31' operates similarly to the analog switch 31 of FIG. 2 but in a reversed manner, and thus controls the passage of the output signal $V_A$ from the first amplifier 11 in response to the digital output signal $V_D$ from the second amplifier 12 imposed upon the control terminal thereof in the following manner. That is, when the digital output signal $V_D$ is high, the analog switch 31' is closed to allow the analog output signal $V_A$ from the first amplifier 11 to flow into ground through the now conductive analog switch 31', whereas when the output signal $V_D$ is low, the analog switch 31' is opened, allowing the analog output signal $V_A$ from the first amplifier 11 to be supplied to the buffer amplifier 33'.

Although some examples of the signal mixer 3 are illustrated in FIGS. 2 and 3, it is not limited to these examples but may take other forms.

Figure 4:
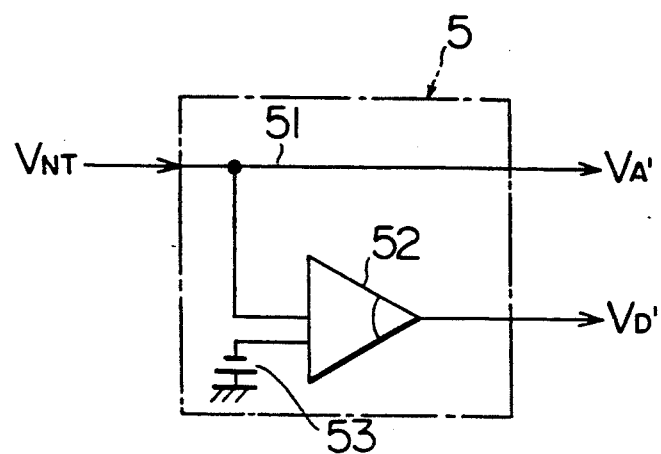

FIG. 4 shows a concrete example of the signal separator 5. The signal separator 5 of this example has a single input terminal connected to receive the mixed output signal $V_{NT}$ from the signal mixer 3 and a pair of first and second output terminals for outputting an analog component $V_A'$ and a digital component $V_D'$, respectively, to the refractive index modifying means 6. The separator 5 includes a signal line 51 connected between the input terminal and the first output terminal for passing an analog component $V_A'$ in the mixed signal $V_{NT}$, and a comparator 52 which has a first input terminal connected to the signal line 51, a second input terminal to which a reference voltage in the form of a threshold is supplied by a reference power supply 53, and an output terminal connected to the second output terminal. The comparator 52 compares the mixed signal $V_{NT}$ with the prescribed reference voltage o threshold supplied from the reference power supply 53 and generates an output signal $V_D'$ in the form of a digital component $V_D'$ when the former is higher than the latter. The analog component $V_A'$ and the digital component $V_D'$ output from the signal separator 5 at the first and second output terminals correspond to the refractive index signal $V_N$ and the temperature signal $V_T$, respectively.

Figure 6:
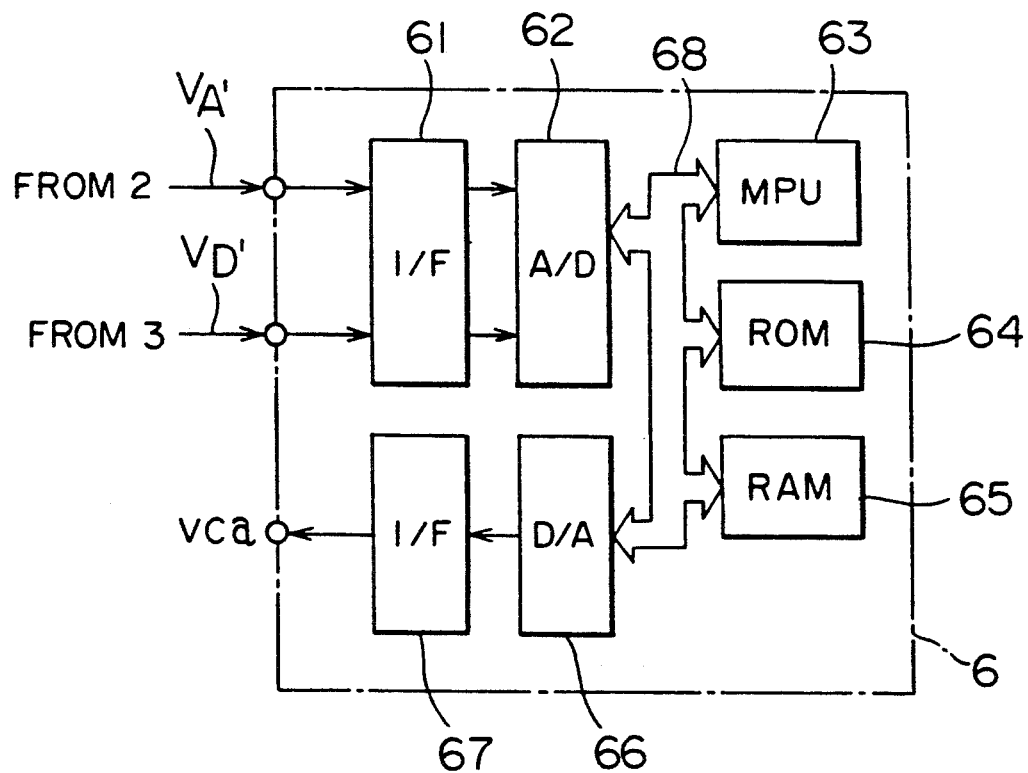
FIG. 6 is a waveform diagram showing one example of the waveform of a mixed signal generated by the signal mixer of FIG. 1.

As illustrated in FIG. 6, the refractive index modifying means 6 comprises an input interface 61 having an analog input port and a digital input port connected to receive the analog component $V_A'$ and the analog component $V_D'$ from the signal separator 5, an A/D converter 62 for converting the analog and digital component $V_A'$, $V_D'$ from analog into analog form, a microprocessor unit 63 (hereinafter referred to as an MPU) for performing operational calculations, a ROM 64 for storing various programs to be performed by the microprocessor 63 as well as data, information, a RAM 65 for temporally storing the results of calculations performed by the MPU 63, etc., a digital-to-analog (D/A) converter 66 for converting digital signals or values calculated and output by the microprocessor unit 63 from digital to analog form, an output interface 67 for outputting the analog signal $V_{Ca}$ from the D/A converter 66 to an external device (no shown), and a signal transmission bus 68 for transmitting signals between the A/D converter 62, the MPU 63, the ROM 64, the RAM 65 and the D/A converter 66. The ROM 64 also stores a first reference refractive index $ND_{ao}$ of a first liquid component and a second reference refractive index $ND_{go}$ of a second liquid component, as well as first and second modification coefficients $\alpha a$, $\alpha g$ for the first and second liquid components, respectively. The MPU 63 calculates the first and second refractive indexes $ND_a$, $ND_g$ of the first and second liquid components at the temperature of TF sensed by the temperature sensor 2 on the basis of the first and second reference refractive indexes $ND_{ao}$, $ND_{go}$ as well as the first and second modification coefficients $\alpha a$, $\alpha g$, and further calculates the contents of respective liquid components based on the thus calculated first and second refractive indexes $ND_a$, $ND_g$.

The operation of the above-described embodiment of FIGS. 1 through 6 will now be described in detail with particular reference to FIG. 5.

As described above, on the basis of the analog output signals $V_N$, $V_T$ from the refractive index sensor 1 and the temperature sensor 2, the signal mixer 3 generates a mixed signal $V_{NT}$ containing an analog component $V_A$ corresponding to one of the analog output signals $V_N$, $V_T$ and a digital component $V_D$ corresponding to the other thereof. Here, let us consider the case that the analog and digital components $V_A$, $V_D$ correspond to the refractive index signal $V_N$ and the temperature signal $V_T$, respectively.

First, the refractive index sensor 1 and the temperature sensor 2 generate refractive index signal $V_N$ in analog form representative of the refractive index of a fuel and a temperature signal $V_T$ in analog form representative of the temperature of the fuel. These output signals $V_N$, $V_T$ are input to the signal mixer 3 where the first amplifier 11 generates an analog signal $V_A$ having an amplitude equal to that of the output signal $V_N$ from the refractive index sensor 1 and the second amplifier 12 converts the temperature signal V: from analog into digital form to generate a digital signal $V_a$ in the form of a square pulse having a period or a duty ratio corresponding to the magnitude of the temperature signal $V_T$.

In the case of the mixer S of FIG. 2, the analog signal $V_A$ from the first amplifier 11 is fed to the input terminal of the analog switch 31, whereas the digital signal $V_D$ from the second amplifier 12 is imposed upon the control terminal of the analog switch 31. If the digital signal $V_D$ is high, the analog switch 31 is closed or turned on, passing and outputting at its output terminal the analog signal $V_A$ as it is input thereto. Contrarily, if the digital signal $V_D$ is low, the analog switch 31 is opened or turned off so that the output terminal of the analog switch 31 connected through the resistor 32 to ground is cut off from the analog signal $V_A$, making the level of its output signal $V_{NT}$ fall to near a ground level.

Figure 5:
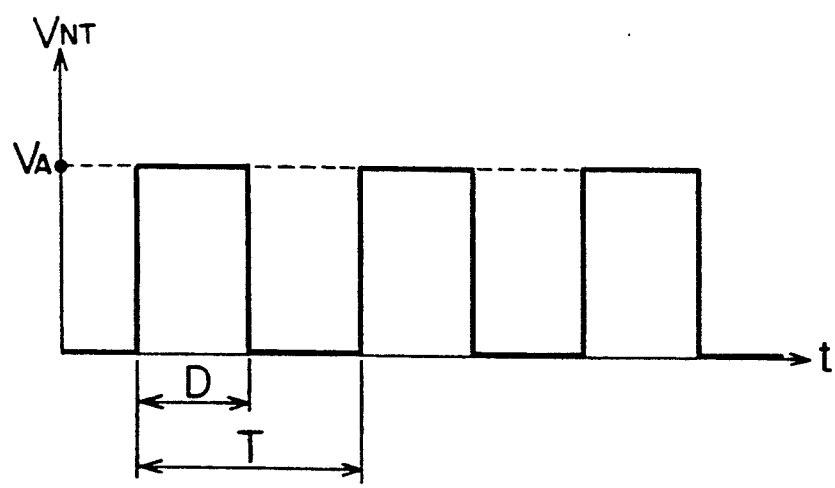
FIG. 5 is a circuit diagram of one example of a signal separator of FIG. 1.

Accordingly, as illustrated in FIG. 5, the mixed signal $V_{NT}$ takes a wave form having a pulse width D and a period T corresponding to those of the digital signal $V_D$, as well as an amplitude corresponding to that of the analog signal $V_A$. In this case, the amplitude $V_A$ of the mixed signal $V_{NT}$ represents the refractive index of the fuel sensed by the refractive index sensor 1, and the period T or the duty ratio (D/T) of the pulse width D to the period T of the mixed signal $V_{NT}$ represents the temperature of the fuel sensed by the temperature sensor 2.

On the other hand, in the case of the signal mixer 3 of FIG. 3, the analog signal $V_A$ from the first amplifier 11 is supplied through the resistor 32' to the respective input terminals of the analog switch 31' and the buffer amplifier 33'. The digital signal $V_D$ from the second amplifier 12 is imposed upon the control terminal of the analog switch 31'. Thus, when the digital signal $V_D$ is high, the analog switch 31' is closed or turned on, allowing the analog signal $V_A$ from the first amplifier 11 to flow to ground through the resistor 32' and the now conductive analog switch 31'. As a result, the analog signal $V_A$ is not supplied to the buffer amplifier 33'. In contrast, when the digital signal $V_D$ is low, the analog switch 31' is opened or turned off so that the analog signal $V_A$ is supplied through the resistor 32' to the buffer amplifier 33' which generates a mixed signal $V_{NT}$ having a wave form substantially simi)ar to that of FIG. 5.

The mixed signal $V_{NT}$ having the refractive index signal $V_N$ and the temperature signal $V_T$ thus superposed on each other is fed as a single signal to the ECU 4, but before being input to the refractive index modifying means 6, it must be separated into an analog component $V_A'$ corresponding to the refractive index signal $V_N$ and a digital component $V_D'$ corresponding to the temperature signal $V_T$. The signal separator 5 serves for this purpose. That is, the signal separator 5 serves, on one hand, to pass and supply the mixed signal $V_{NT}$ directly to the analog input port of the input interface 61 of the refractive index modifying means 6 as an analog component $V_A'$: and, on the other hand, supply it to a digital input port of the input interface 61 of the refractive index modifying means 6 as a digital component $V_D'$ through the comparator 52. In this connection, the comparator 52 extracts only the digital component $V_D'$ from the mixed signal $V_{NT}$, as referred to before. In this manner, the mixed signal $V_{NT}$ from the signal mixer 3 is input as a single signal to the ECU 4.

The A/D converter 62 of the refractive index modifying means 6 receives through the input interface 61 the analog and digital components $V_A'$, $V_D'$ separately, and converts the amplitude of the analog signal $V_A'$ representative of the refractive index of the fuel from analog into digital form, which is then read into the MPU 63. Also, the digital component $V_D'$ is read through the input interface 61 and the A/D converter 62 into the MPU 63 where the period T or the duty ratio (D/T) of the pulse width D to the period T of the digital component $V_D'$ (FIG. 5) representative of the sensed temperature of the fuel is calculated.

Figure 7:
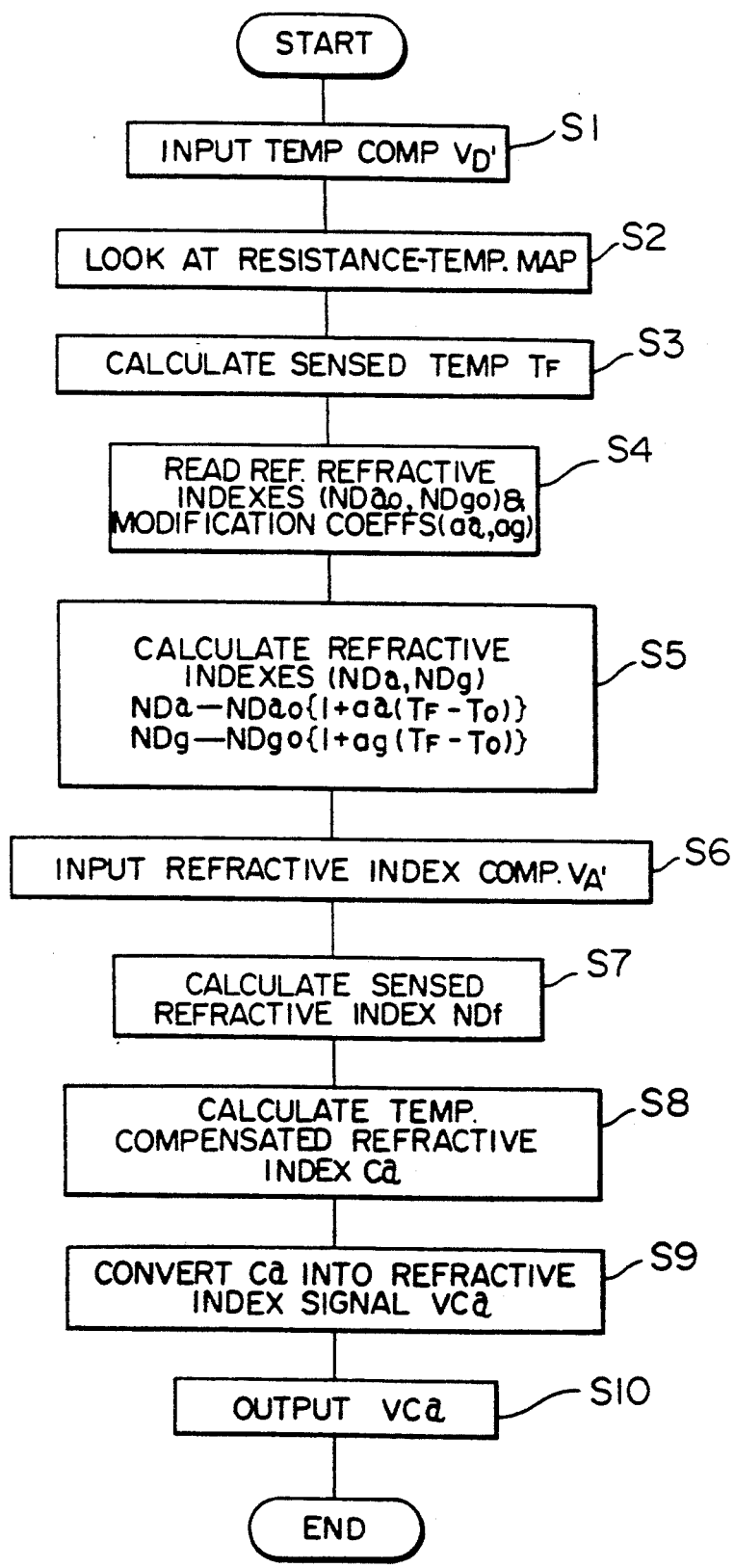
FIG. 7 is a flow chart showing the operation of the refractive index modifying means of FIG. 6.
Figure 16:
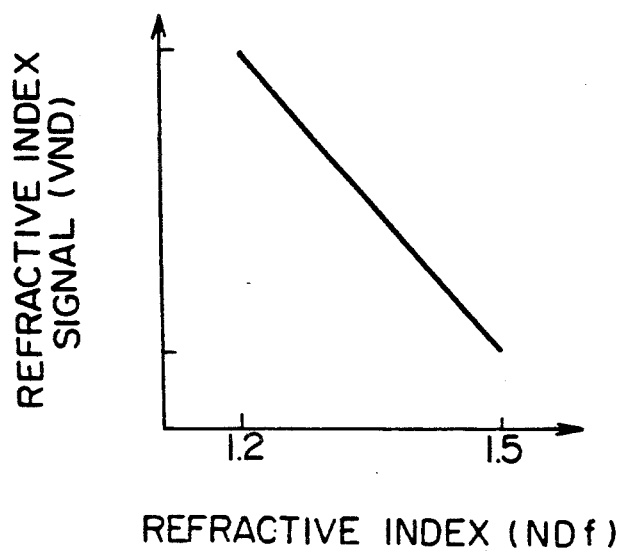
FIG. 16 is a diagram showing the relationship between a refractive index NDf of a liquid to be detected and a refractive index signal VND from a refractive index calculator of FIG. 15.

Specifically, as shown in the flow chart of FIG. 7, the MPU 63 calculates the content $C_a$ of a liquid component in the fuel as follows. In this case, let us suppose that the fuel to be detected comprises gasoline and alcohol, and that the ROM 64 stores maps or graphs of FIGS. 16 through 18. First, the analog component $V_A'$ corresponding to the refractive index signal $V_N$ and the digital component $V_D'$ corresponding to the temperature signal $V_T$ from the signal separator 3 are input to the input interface 61 where they are changed into voltage levels suitable for the analog to digital conversion by the A/D converter 62. Then, based on a temperature modifying program as shown in the flow chart of FIG. 7 and stored in the ROM 64, the analog component $V_A'$ after being converted into digital form by the A/D converter 62 and the digital component $V_D'$ from the signal separator 5 are taken into the MPU 63 where the digitized analog component $V_A'$ representative of the refractive index of the fuel is compensated for the fuel temperature based on the digital component $V_D'$ representative of the temperature of the fuel so as to provide the content of alcohol in digital form which is then converted into analog form by the D/A converter 66 and output as an alcohol content signal $V_{Ca}$ to an external device (not shown) such as an engine controller through the output interface 67.

Figure 17:
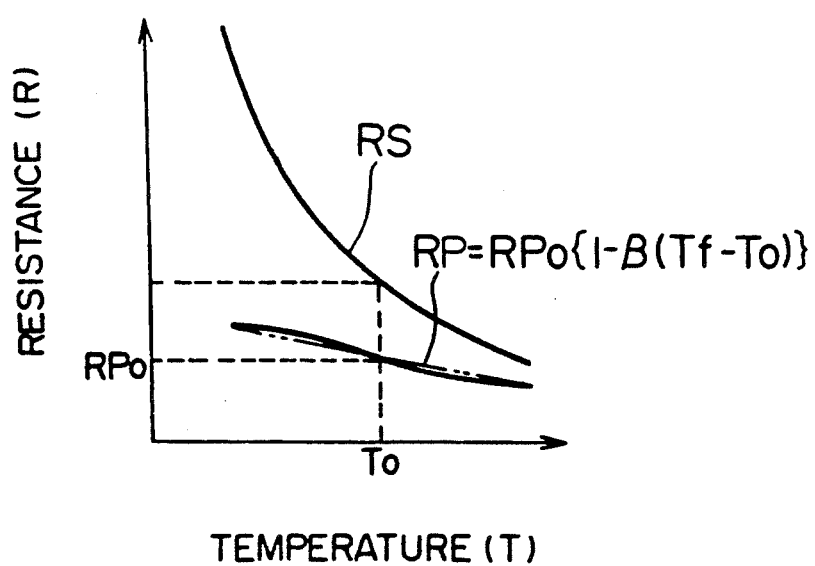
FIG. 17 is a diagram showing the relationships between the temperature T and the resistance RS of a temperature sensor of FIG. 15 as well as between the temperature T and the total resistance RP of the temperature sensor and a resistor connected in parallel thereto.
Figure 18:
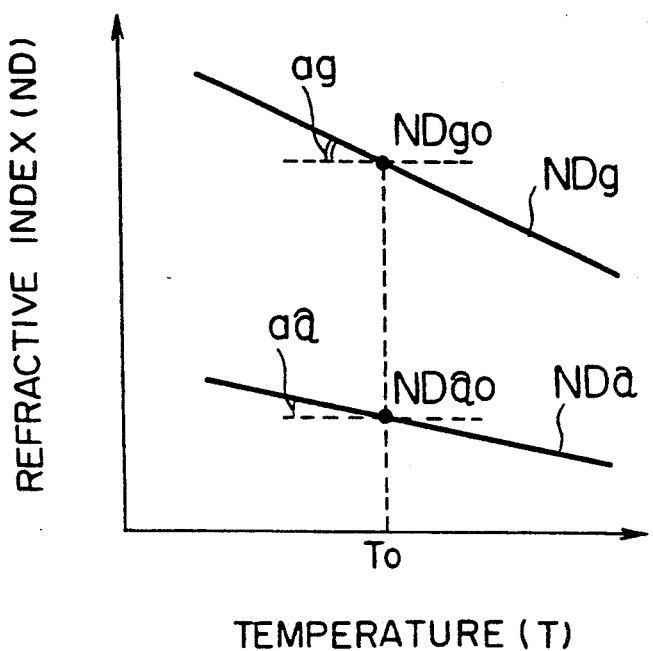
FIG. 18 is a diagram showing the temperature dependencies of the refractive indexes NDg, NDα of gasoline and alcohol, respectively.
Figure 19:
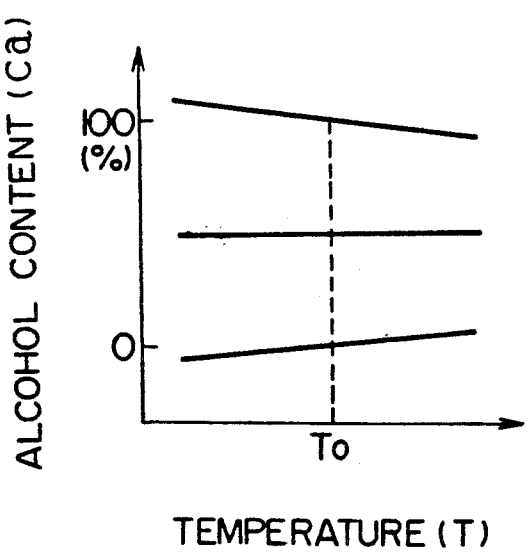
FIG. 19 is a diagram showing the temperature dependency of the alcohol content in gasoline.

More specifically, in Step S1, the analog or temperature component $V_A'$ from the signal separator 5 is input through the input interface 61 and the A/D converter 62 to the MPU 63. Then in Step S2, the MPU 63 reads out from the ROM 64 a resistance-temperature map, as shown in FIG. 17, corresponding to the resistance-temperature characteristic of the temperature sensor 3. In Step S3, based on the digital or temperature component $V_D'$ from the signal separator 5, the MPU 63 calculates the temperature TF of the fuel as sensed by the temperature sensor 2.

Subsequently in Step S4, the reference refractive indexes NDao, NDgo as well as the modification coefficients $\alpha_a$, $\alpha_g$ of alcohol and gasoline at a predetermined reference temperature T° are read out from the ROM 64, and in Step S5, the refractive indexes NDa, NDg of alcohol and gasoline at the sensed temperature TF are calculated based on these indexes and coefficients thus read out. In this connection, the refractive indexes NDa, NDg are expressed as follows:

$$NDa = NDa^\circ\{1 + \alpha a(TF - T^\circ)\}$$

$$NDg = NDg^\circ\{1 + \alpha g(TF - T^\circ)\}$$

In Step S6, the analog or refractive index component $V_A'$ from the signal separator 5 is fed through the input interface 61 to the A/D converter 62 where it is converted from analog into digital form and then input to the MPU 63. In Step S7, the MPU 63 converts the digitized refractive index signal $V_A'$ into a corresponding sensed refractive index NDf while looking at the refractive index map of FIG. 16.

Thereafter in Step S8, on the basis of the sensed refractive index NDf thus converted and the calculated refractive indexes NDa, NDg as obtained in Step S5, the MPU 63 calculates the content of alcohol Ca at the sensed temperature through linear interpolation as follows:

$$Ca = (NDf - NDg)/(NDa - NDg) \qquad (4)$$

Finally in Step S9, the alcohol content Ca thus temperature compensated is converted from digital into analog form by the D/A converter 66 to provide a corresponding alcohol content signal $V_{Ca}$ which is then output from the output interface 67.

Figure 8:
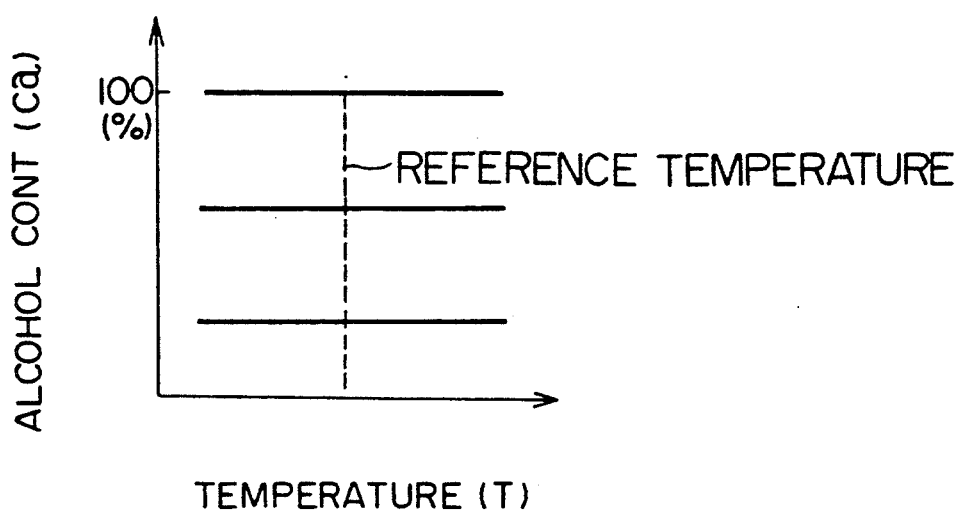
FIG. 8 is a diagram showing the temperature characteristic of the alcohol content.

According to the thus temperature compensated alcohol content signal $V_{Ca}$, the alcohol content Ca finally obtained is temperature compensated and hence made constant irrespective of variations in its temperature, as illustrated in FIG. 8. Accordingly, even if the refractive index NDf of the mixed fuel changes with temperature variations, it is possible to obtain the accurate alcohol content Ca at all times over the entire alcohol content range.

Although in the above embodiment, the ECU 4 is independently provided, it can be incorporated into an engine controller such as a fuel injection control unit which controls the amount of fuel to be injected into cylinders of an engine as well as the injection timing at which fuel is injected into each cylinder. In this case, if the same processing program as shown in FIG. 7 is executed by an MPU in the fuel injection control unit, there is no need to output the calculated alcohol content signal $V_{Ca}$ to an external device, thus making it possible to omit the D/A converter 66 and the output interface 67.

Figure 9:
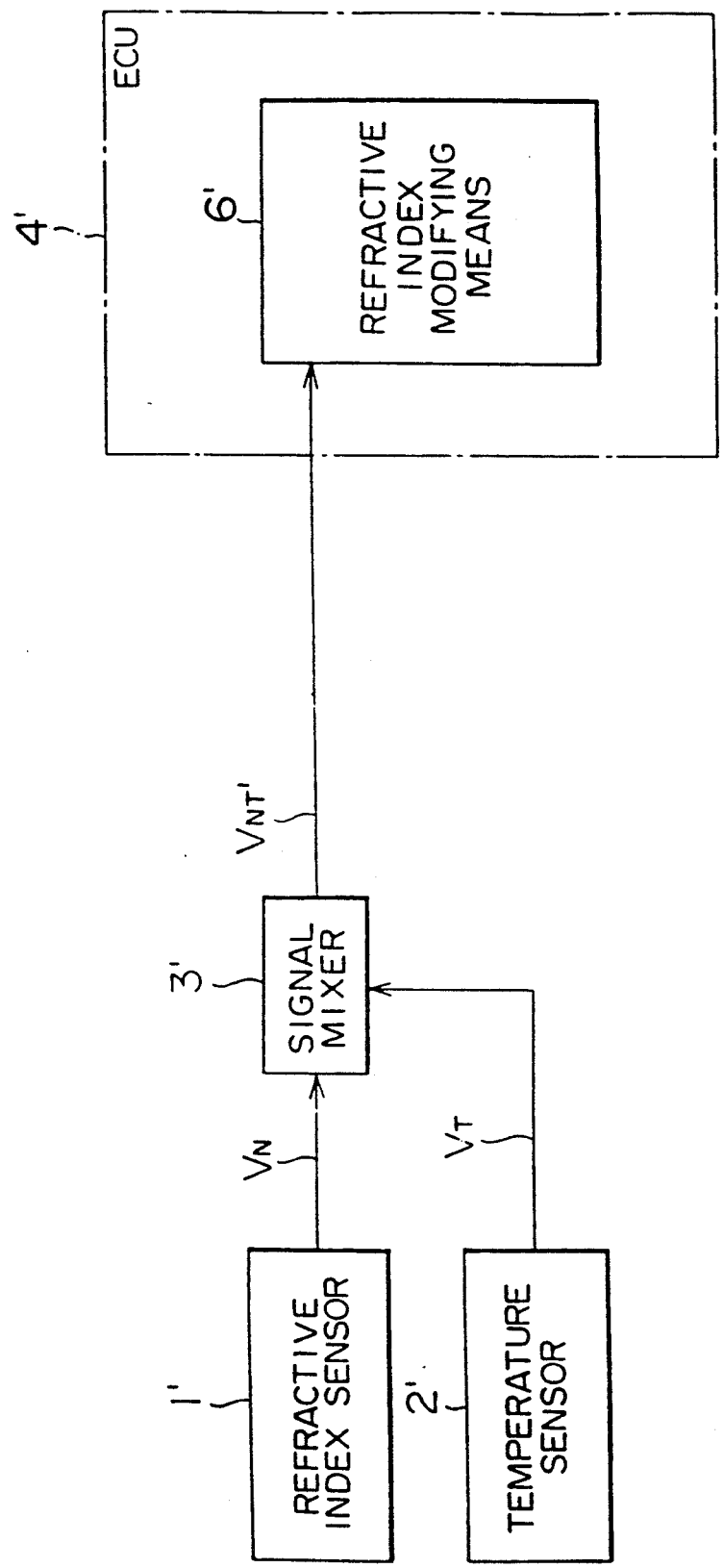
FIG. 9 is a view similar to FIG. 1, but showing another embodiment of the invention.

Although in the above embodiment, the refractive index signal $V_N$ and the temperature signal $V_T$ are mixed with or superposed on each other as the analog component and the digital component, they may be mixed with or superposed on each other as digital signals, as illustrated in FIG. 9.

FIG. 9 shows a liquid content detecting apparatus in accordance with another embodiment of the invention. The apparatus of this embodiment includes, in addition to a refractive index sensor 1' and a temperature sensor 2' which are the same as those of FIG. 1, a signal mixer 3' and a liquid content calculator 4' in the form of an ECU which are different from the corresponding elements 3, 4 of FIG. 1. The signal mixer 3' operates to superpose the refractive index signal $V_N$ and the temperature signal $V_T$ both in digital form one over another to provide a mixed signal $V_{NT}'$. The liquid content calculator 4' comprises a refractive index modifying means 6' which has a single input port for receiving the single mixed signal $V_{NT}'$ from the signal mixer 3'.

Figure 10:
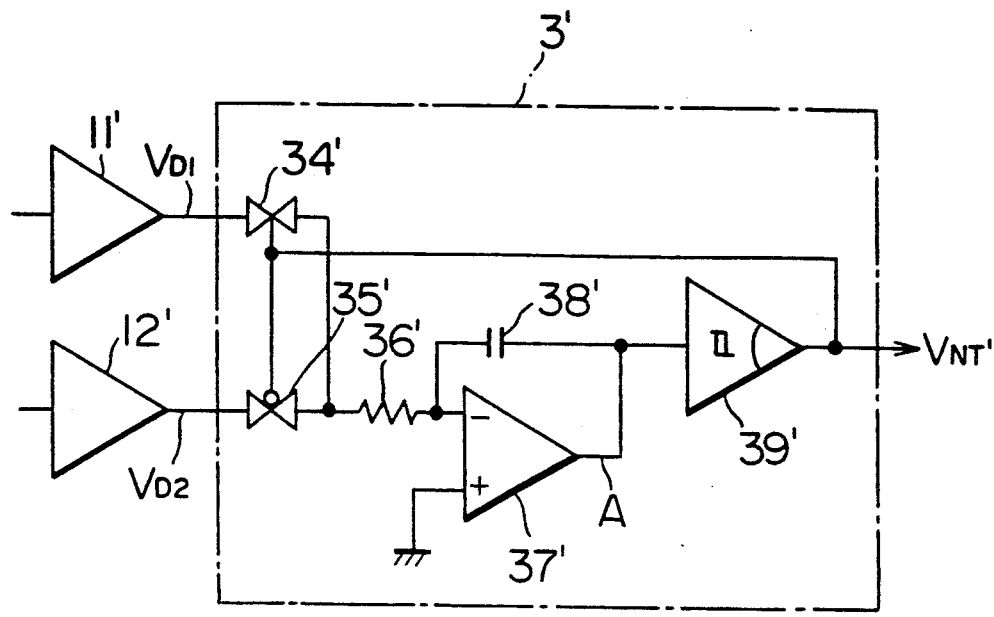
FIG. 10 is a circuit diagram of a concrete example of a signal mixer of FIG. 9.

FIG. 10 shows a concrete example of the signal mixer 3' of FIG. 9. The signal mixer 3' of this example includes a first amplifier 11' for receiving the refractive index signal $V_N$ in analog form from the refractive index sensor 1' and converting it into a first digital signal $V_{D1}$, and a second amplifier 12' for receiving the temperature signal $V_T$ from the temperature sensor 2' in analog form and converting it into a second digital signal $V_{D2}$. The first and second digital signals $V_{D1}$, $V_{D2}$ are opposite in polarity from each other. For example, the first digital signal VD1 is positive while the second digital signal VD2 is negative or vice versa.

The signal mixer 3' further includes a pair of first and second analog switches 34', 35' which have their input terminals connected to receive the first and second digital signals VD1, VD2, respectively, from the first and second amplifiers 11', 12', and their output terminals coupled together, and their control terminals coupled to each other. An operational amplifier 37' has a first negative or inverted input terminal connected through a resistor 36' to the output terminals of the first and second analog switches 34', 35', a second positive or non-inverted input terminal connected to ground, and an output terminal connected through a capacitor 38' to the first inverted input terminal thereof. A comparator 39' has an input terminal connected to a junction between the output terminal of the operational amplifier 37' and the capacitor 38' for receiving an output signal A from the operational amplifier 37' which is integrated by the capacitor 38', and an output terminal connected to the control terminal of the first analog switch 34' and to the inverted control terminal of the second analog switch 35' so that the first and second analog switches are alteratively opened and closed by the output signal from the comparator 39'. The comparator 39' has an upper threshold and a lower threshold so that it serves to invert, with hysteresis or a certain delay, the integrated output signal A from the operational amplifier 37' when the integrated signal A rises above the upper threshold or falls below the lower threshold, so as to provide a mixed signal $V_{NT}'$.

Figure 11:
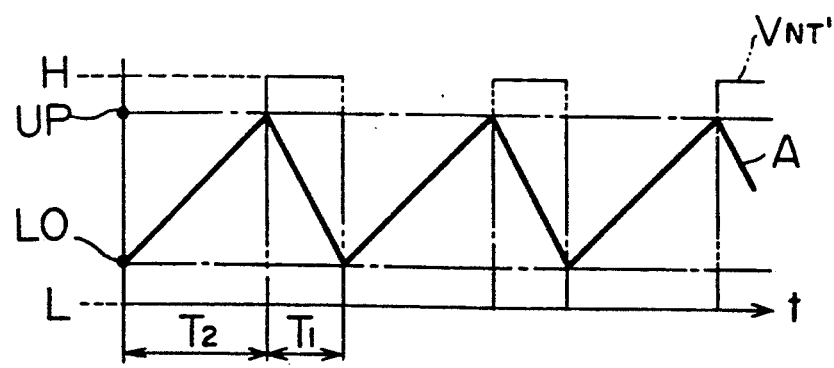
FIG. 11 is a waveform diagram showing the operation of the signal mixer of FIG. 10.

FIG. 11 diagrammatically shows the relationship between the integrated signal A from the operational amplifier 37', designated by the solid line, and the mixed signal $V_{NT}'$ output from the comparator 39', designated by the phantom line. In this figure, reference symbol T1 represents the pulse width of a high level pulse; T2 the pulse width of a low level pulse; H, L a high level and a low level, respectively; and UP, LO the higher threshold and the lower threshold, respectively, of the comparator 39'.

Figure 12:
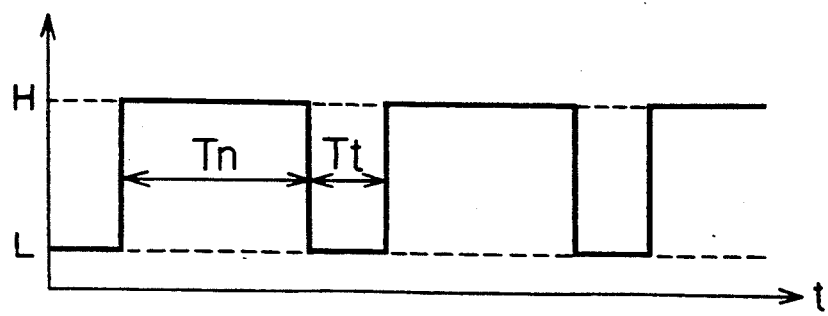
FIG. 12 is a waveform diagram showing the waveform of a mixed signal generated by the signal mixer of FIG. 10.
Figure 13:
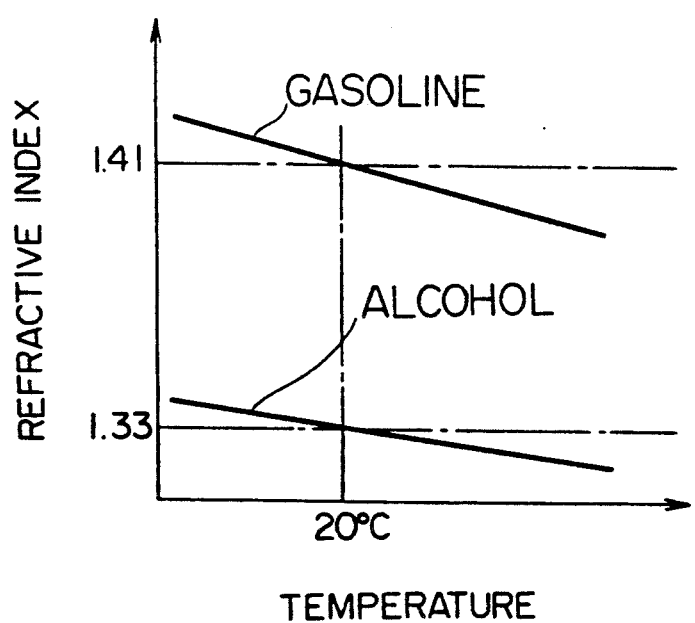
FIG. 13 is a diagram showing the relationships between the temperature and the refractive indexes of gasoline and alcohol.

FIG. 12 diagrammatically shows the wave form of the mixed signal $V_{NT}'$ analyzed by the refractive index modifying means 6'. In this figure, the pulse width Tn of a high level pulse (e.g., corresponding to the refractive index signal $V_N$) corresponds to the pulse width T2 of a low level pulse of FIG. 11, and the pulse width Tt of a low level pulse (e.g., corresponding to the temperature signal $V_T$) corresponds to the pulse width T1 of a high level pulse of FIG. 11.

The operation of the second embodiment as illustrated in FIGS. 9 and 10 will now be described in detail with particular reference to the waveform diagrams of FIGS. 11 and 12.

If the mixed signal $V_{NT}'$ from the comparator 39' is low, the first analog switch 34' is opened and the second analog switch 35' is closed so that a second digital signal VD2 of negative polarity from the temperature sensor 2' is input to the first inverted input terminal of the operational amplifier 37'. As a result, the operational amplifier 37' generates an output signal in the form of the digital signal VD2 which is integrated by the capacitor 36' as a function of time to provide an integrated signal A, as clearly shown in FIG. 11, which increases at a rate or slope proportional to the amplitude of the second digital signal VD2. At this time, the threshold level of the comparator 39' is set to the upper threshold UP so that the mixed signal $V_{NT}'$ from the comparator 39' remains at a low level until the integrated signal A from the operational amplifier 37' exceeds the upper threshold UP.

When the integrated signal A increases to reach the upper threshold UP after the lapse of a time T2 from the start of integration, the output signal $V_{NT}'$ from the comparator 39' turns into a high level. Thus, the low level period of the mixed signal $V_{NT}'$ continues for a period of time T2 which is in inverse proportion to the magnitude of the second digital signal VD2.

When the mixed signal $V_{NT}'$ becomes high, the threshold level of the comparator 39' is set to the lower threshold LO, and at the same time the second analog switch 35' is opened and the first analog switch 34' is closed so that the first digital signal VD1 of positive polarity from the refractive index sensor 1' is input to the first inverted input terminal of the operational amplifier 37'. As a result, the output signal A from the amplifier 37' integrated by the capacitor 38' decreases at a rate or slope proportional to the magnitude of the first digital signal VD1, and continues to be integrated as a function of time until it reaches the lower threshold LO. Accordingly, the high level period of the mixed signal $V_{NT}'$ continues for a period of time T1 which is in inverse proportion to the magnitude of the first digital signal VD1.

For example, the mixed signal $V_{NT}'$ thus obtained takes a wave form which has a low level period T2 corresponding to the inverse of the refractive index signal $V_N$, and a high level period T1 corresponding to the inverse of the temperature signal $V_T$.

Accordingly, the refractive index modifying means 6' reads in from its single input port the mixed signal $V_{NT}'0$ from the comparator 39' and analyzes it to provide a pulse signal of a wave form which has a high level period Tn corresponding to the refractive index signal $V_N$ and a low level period Tt corresponding to the temperature signal $V_T$.

The use of the mixed signal $V_{NT}'$, which has the first and second digital signals VD1, VD2 superposed one over the other in this manner, can not only omit a signal separator as employed in the first embodiment of FIG. 1, but also requires only a single input port for the refractive index modifying means 6'. This serves to simplify the overall arrangement of the liquid content detecting apparatus.

Although in the above embodiment of FIGS. 9 and 10, the refractive index signal $V_N$ and the temperature signal $V_T$ correspond to the durations T1, T2, respectively, of the high and low levels of the mixed signal $V_{NT}'$, they may instead correspond to the period and the duty ratio of the mixed signal $V_{NT}'$. In this case, as seen from FIG. 12, the period T is equal to the sum of the pulse widths Tn, Tt, and the duty ratio Dr is expressed as follows:

$$Dr = Tn/(Tn + Tt)$$

Accordingly, the refractive index signal $V_N$ and the temperature signal $V_T$ can be separately read into the refractive index modifying means 6'.

In addition, the refractive index signal $V_N$ and the temperature signal $V_T$ may correspond to the rising and falling periods, respectively, of the mixed signal $V_{NT}$.

Further, although in the above embodiments, the refractive index sensor 1, 1' is of the photoelectric type sensing the amount of light received, it can be of the position sensitive type sensing the position of light received which varies depending upon variations in the refractive index of a liquid t be detected.

Moreover, the mixed fuel comprises a first liquid in the form of alcohol) and a second liquid in the form of gasoline, but it may comprise any two kinds of liquids other than the above which are different in their refractive-index versus temperature characteristics.

What is claimed is:

1. A liquid content detecting apparatus for detecting the content of a liquid component contained in a mixed liquid, said apparatus comprising:
   a refractive index sensor for sensing the refractive index of a liquid component in the mixed liquid and generating a corresponding refractive index signal;
   a temperature sensor for sensing the temperature of the mixed liquid and generating a corresponding temperature signal;
   a signal mixer coupled to the refractive index sensor and the temperature sensor for mixing the refractive index signal and the temperature signal with each other to generate a single mixed signal; and
   a liquid content calculator coupled to the signal mixer for calculating the content of the liquid component based on the single mixed signal.

2. A liquid content detecting apparatus according to claim 1, wherein the refractive index signal and the temperature signal are both of analog form, and wherein said signal mixer comprises:
   a first operational amplifier connected to receive one of the refractive index signal from said refractive index sensor and the temperature signal from said temperature sensor, said first operational amplifier being operable to maintain the analog form of the signal received;
   a second operational amplifier connected to receive the other of the refractive index signal and the temperature signal for converting the other signal from analog into digital form; and
   an analog switch having an input terminal connected to said first operational amplifier, a control terminal connected to said second operational amplifier, and an output terminal connected to said liquid content calculator, said analog switch being opened and closed by a digital signal output from said second operational amplifier.

3. A liquid content detecting apparatus according to claim 1, wherein the refractive index signal and the temperature signal are both of analog form, and wherein said signal mixer comprises:
   a first operational amplifier connected to receive one of the refractive index signal from said refractive index sensor and the temperature signal from said temperature sensor, said first operational amplifier being operable to maintain the analog form of the signal received;
   a second operational amplifier connected to receive the other of the refractive index signal and the temperature signal for converting the other signal from analog into digital form;
   a third amplifier having an input terminal connected through a resistor to said first operational amplifier and an output terminal connected to said liquid content calculator; and
   an analog switch connected to a node between said resistor and said third amplifier, a control terminal connected to said second operational amplifier, and an output terminal connected to ground, said analog switch being opened and closed by a digital signal output from said second operational amplifier so as to permit and interrupt the transmission of the analog signal from the first operational amplifier to the third amplifier.

4. A liquid content detecting apparatus according to claim 1, wherein said liquid content calculator comprises:
   a signal separator for generating a refractive index component corresponding to the refractive index signal and a temperature component corresponding to the temperature signal; and
   refractive index modifying and liquid content calculating means for modifying the sensed refractive index of the liquid from said refractive index sensor based on the temperature signal from said temperature sensor to provide a temperature compensated refractive index of the liquid, said refractive index modifying and liquid content calculating means being operable to calculate the content of each liquid component based on the temperature compensated refractive index.

5. A liquid content detecting apparatus according to claim 4, wherein said signal separator has a single input terminal connected to receive the mixed signal from said signal mixer, a first output terminal directly connected to the input terminal through a signal line for outputting the mixed signal as an analog component, and a second output terminal connected to the input terminal through a comparator, said comparator generating a digital component depending upon whether the mixed signal is higher or lower than a prescribed threshold.

6. A liquid content detecting apparatus according to claim 1, wherein said signal mixer comprises:
   a first amplifier for receiving the refractive index signal in analog form from said refractive index sensor and converting it into a first digital signal;
   a second amplifier for receiving the temperature signal in analog form from said temperature sensor and converting it into a second digital signal, the first and second digital signals being opposite in polarity from each other;
   a first analog switch having an input terminal connected to receive the first digital signal from said first amplifier, an output terminal and a control terminal;
   a second analog switch having an input terminal connected to receive the second digital signal from said second amplifier, an output terminal and a control terminal;
   an operational amplifier having a first inverted input terminal connected through a resistor to the output terminals of said first and second analog switches, a second non-inverted input terminal connected to ground, and an output terminal connected through a capacitor to the first inverted input terminal thereof; and
   a comparator having an input terminal connected to a junction between the output terminal of said operational amplifier and said capacitor for receiving an output signal from said operational amplifier which is integrated by said capacitor, and an output terminal connected to the control terminal of said first analog switch and to the control terminal of said second analog switch through an inverter so that said first and second analog switches are alternatively opened and closed by the output signal from said comparator, said comparator having an upper threshold and a lower threshold so that it serves to invert, with hysteresis, the integrated output signal from said operational amplifier so as to he within a range between the upper and lower thresholds, to provide a mixed signal.

7. A liquid content detecting apparatus according to claim 4, wherein said refractive index modifying means comprises:

memory means for storing a reference refractive index and a modification coefficient at a predetermined reference temperature for each of the liquid components;

refractive index calculating means for calculating the refractive index of each liquid component at the temperature of the liquid as sensed by said temperature sensor using the reference refractive index and the modification coefficient at the predetermined temperature for the corresponding liquid component; and interpolation means for calculating an actual refractive index of each liquid component based on the primary refractive index thereof sensed by said refractive index sensor and the estimated refractive index thereof calculated by said refractive index calculating means.

8. A liquid content detecting method for detecting the content of liquid components contained in a liquid, said method comprising the steps of:

sensing the temperature of the liquid and generating a corresponding temperature signal;

sensing the refractive index of the liquid and generating a corresponding refractive index signal;

reading a reference refractive index and a modification coefficient at a predetermined temperature for each liquid component of the liquid;

calculating the temperature compensated refractive index of each liquid component at the sensed temperature of the liquid on the basis of the reference refractive index and the modification coefficient therefor thus read; and calculating the content of each liquid component based on the temperature compensated refractive index thereof.

* * * * *